US00PP18321P2

(12) United States Plant Patent
Glenn

(10) Patent No.: US PP18,321 P2
(45) Date of Patent: Dec. 18, 2007

(54) WILLOW OAK TREE NAMED 'QPSTB'

(50) Latin Name: *Quercus phellos*
Varietal Denomination: QPSTB

(75) Inventor: Michael M. Glenn, Bogart, GA (US)

(73) Assignee: Tree Introductions, Inc., Bishop, GA (US)

( * ) Notice: Subject to any disclaimer, the term of this patent is extended or adjusted under 35 U.S.C. 154(b) by 93 days.

(21) Appl. No.: 11/305,255

(22) Filed: Dec. 15, 2005

Related U.S. Application Data

(63) Continuation of application No. 10/791,963, filed on Mar. 2, 2004, now abandoned.

(51) Int. Cl.
*A01H 5/00* (2006.01)

(52) U.S. Cl. ..... Plt./216

(58) Field of Classification Search ..... Plt./216
See application file for complete search history.

*Primary Examiner*—Wendy Haas
(74) *Attorney, Agent, or Firm*—Klarquist Sparkman, LLP

(57) ABSTRACT

A Willow Oak tree named 'QPSTB' having a dense canopy, dominant central leader, unique red fall color, and relatively fast growth rate, and also capable of being reproduced reliably using softwood cutting methods.

7 Drawing Sheets

Latin name of genus and species: *Quercus phellos.*
Variety denomination: 'QPSTB'.

BACKGROUND OF THE INVENTION

The present invention relates to a new and distinct variety of *Quercus phellos,* Willow Oak, which has been given the varietal name 'QPSTB.'

The original tree of this new Willow Oak variety was discovered in 2001 as a chance seedling growing in a cultivated area of a nursery in Oconee County, Ga. It had been purchased as a 12 to 18 inch liner in spring 1995 and at that time planted in a liner field. This tree was transplanted to another field in spring 1997, where it was subsequently discovered in 2001. In December 2003, this tree was transplanted to an observation area where it has remained since that time. It is now 10 years old from a seed. The description of this new Willow Oak variety is based on observations of this original tree and of asexually propagated progeny, produced from softwood cuttings that are being grown at a nursery in Oconee County, Ga.

Common Willow Oak trees are typically a large deciduous tree with a dense, oblong-oval to rounded crown at maturity. On average, it will reach 40 to 60 feet high and 30 to 40 feet wide at maturity, though the largest trees may reach 100 feet in height with an equal spread. Willow Oaks are native to bottomlands, floodplains and adjacent slopes, and rich uplands from New York to Florida, west to Missouri, Oklahoma and Texas. It prefers moist, well-drained soil but adapts well to harsh conditions, and are therefore one of the best oaks for the heat, drought, and humidity of the Southeast, while still readily adaptable to the more arid Midwest. Willow Oak species are typically hardy in USDA Zones 5–9, perform best in Zones 6–8, and can survive temperatures as low as −25° F. in (such as Cincinnati, Ohio). Insofar as I am aware, Willow Oak trees which are commercially available are grown from seedling material, creating a high degree of variability in the industry, both in landscape situations and nurseries. Seedling Willow Oak trees are variable in growth rate and habit, typically lacks a central leader, and tends to be open in youth.

This new Willow Oak variety is distinguished from other Willow Oaks known to the inventor by the following unique combination of characteristics: dense canopy, dominant central leader, red fall color (very unique for this species), and relatively fast growth rate. When discovered in 2001, the original tree of this new variety was approximately 15% larger than other Willow Oak trees planted at the same time at the same size in the same group of seedlings.

BRIEF SUMMARY OF THE INVENTION

In 2002, the original tree of this new Willow Oak variety was successfully propagated in Oconee County, Ga. by softwood cuttings at my direction. The progeny have demonstrated that the novel characteristics of this new variety are fixed, stable, and reproduce true to type through asexual propagation. These observations confirm that 'QPSTB' represents a new, distinct, and improved variety of Willow Oak as particularly evidenced by the combination of characteristics described above (dense canopy, dominant central leader, unique red fall color, and relatively fast growth rate), which can be asexually propagated reliably using vegetative propagation techniques.

This new variety of Willow Oak is particularly suited for use as a street tree and for filling large areas such as golf courses, commercial sites, and parks. This new Willow Oak variety will provide a uniform, structurally sound tree, and its rapid growth rate will benefit growers who will profit from a faster growing variety of Willow Oak. In addition, my new variety has a unique red fall foliage color. This fall foliage color is absent from common Willow Oak seedlings that have a fall foliage color of yellow, bronze-orange, to yellow-brown.

My new variety differs from another variety of Willow Oak, 'QPSTA' (U.S. Plant Pat. No. 13,677), in that the fall foliage of my new variety is colored red compared to yellow-brown fall foliage color on 'QPSTA'.

BRIEF DESCRIPTION OF THE DRAWINGS

The accompanying photographs depict the color of the tree and foliage of my new variety as nearly true as is reasonably possible to make the same in a color illustration of this character.

DETAILED BOTANICAL DESCRIPTION

This invention has not been observed under all possible environmental conditions. The phenotype may vary with variations in growing environment such as temperature, light intensity, day length, rainfall, or nutrient availability, without, however, any variation in genotype. 'QPSTB' Willow Oak is currently growing at a nursery in Oconee County, Ga. This particular area of Oconee County has a clay loam soil type, is located in USDA Hardiness Zone 7(a), and receives average yearly rainfall of 50 inches (typically ranged between 30 and 60 inches for any given year).

The following is a detailed description of my new variety of Willow Oak with color terminology in accordance with The Royal Horticultural Society (R.H.S.) Colour Chart published by The Royal Horticultural Society in London, England. This description is based on observations of the original tree growing at a nursery site in Oconee County, Ga.

Parentage: Discovered as a chance seedling of unknown origin growing in a cultivated area of a nursery in Oconee County, Ga.

Figure 1:
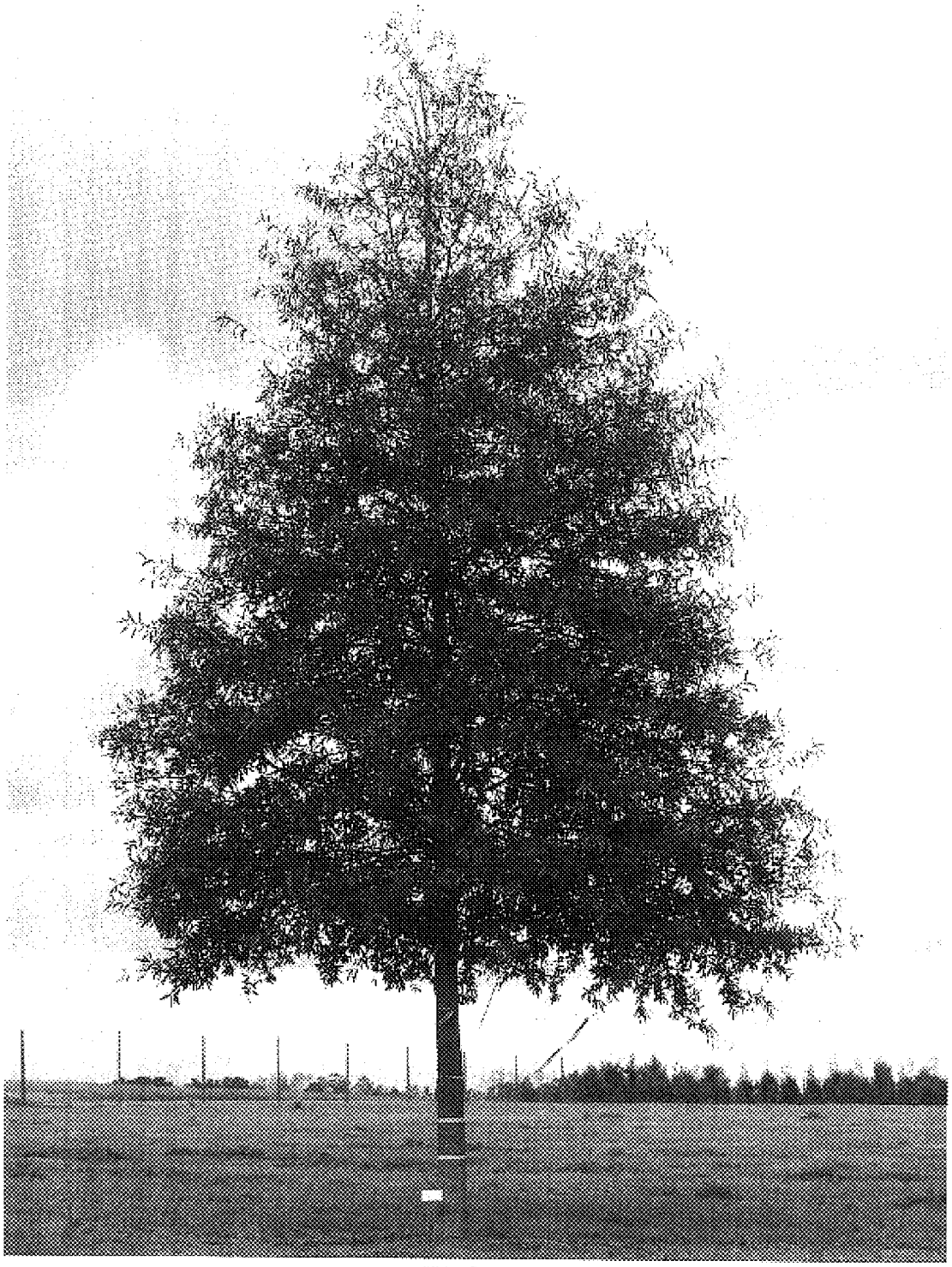
FIG. 1 is a photograph of the original tree of the new variety in fall season leaf.
Figure 2:
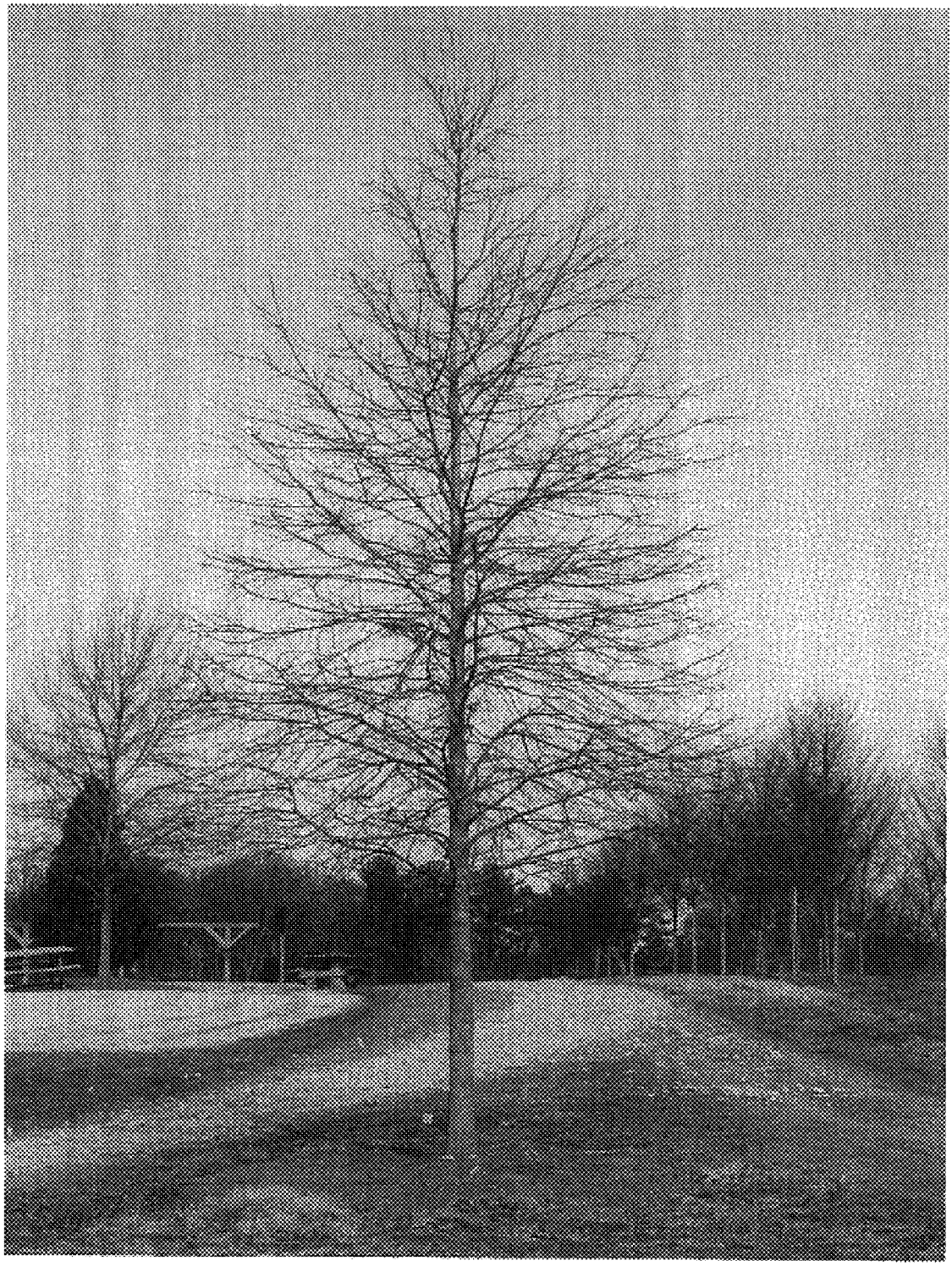
FIG. 2 is a photograph of the original tree of the new variety during winter season.

Tree shape: Dense canopy and a dominant central leader. (See FIGS. 1 and 2).

Tree size: The original tree (11 years old) is about 27 feet high and about 13 feet wide.

Trunk: The trunk is typical of the species with a strong central leader (bole). At about age ten, the initially discovered tree had a diameter of about six inches in diameter measured twelve inches above the ground.

Figure 7:
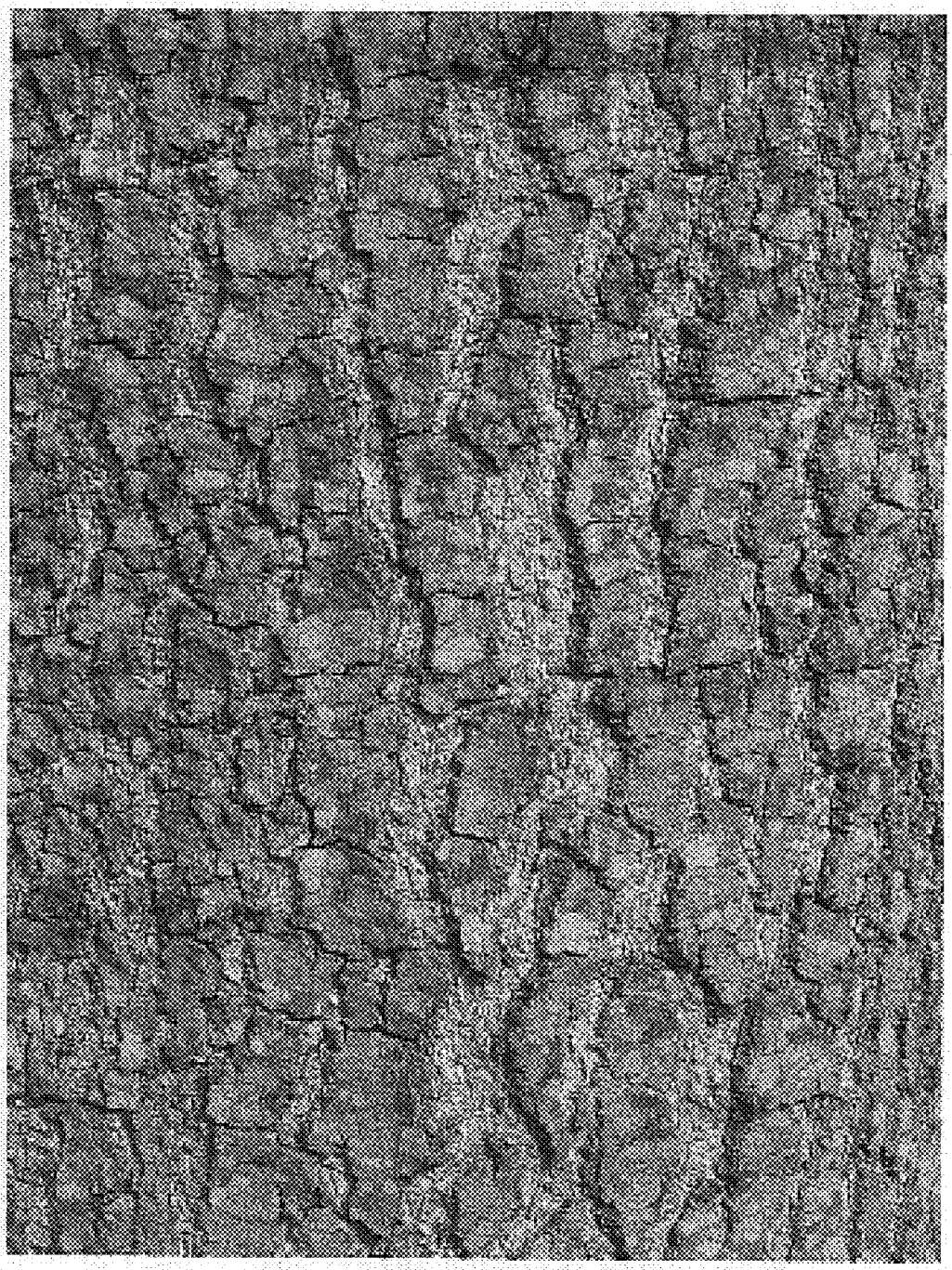
FIG. 7 is a close-up of a typical section of the trunk of the original tree of the new variety.

Bark: Bark is typical of the species, being smooth and gray (RHS 188C) on young trees, and gray (RHS 188C) and, with age, becoming roughened by irregular furrows and thick, more or less scaly ridges (see FIG. 7). Mature bark is grayed green (RHS 198C) in color, also typical of the species.

Branching habit: Denser than typical for the species (See FIGS. 1 and 2). Primary branches toward the top of the tree emerge at about a 45 degree angle to the leader and branch angle relative to the trunk tends to increase with age (see branches on lower portion of tree in FIG. 2).

Branches: One year old (new growth) branches are approximately ¼ inch in diameter with smooth texture and gray-green (RHS 197C) in color.

Figure 3:
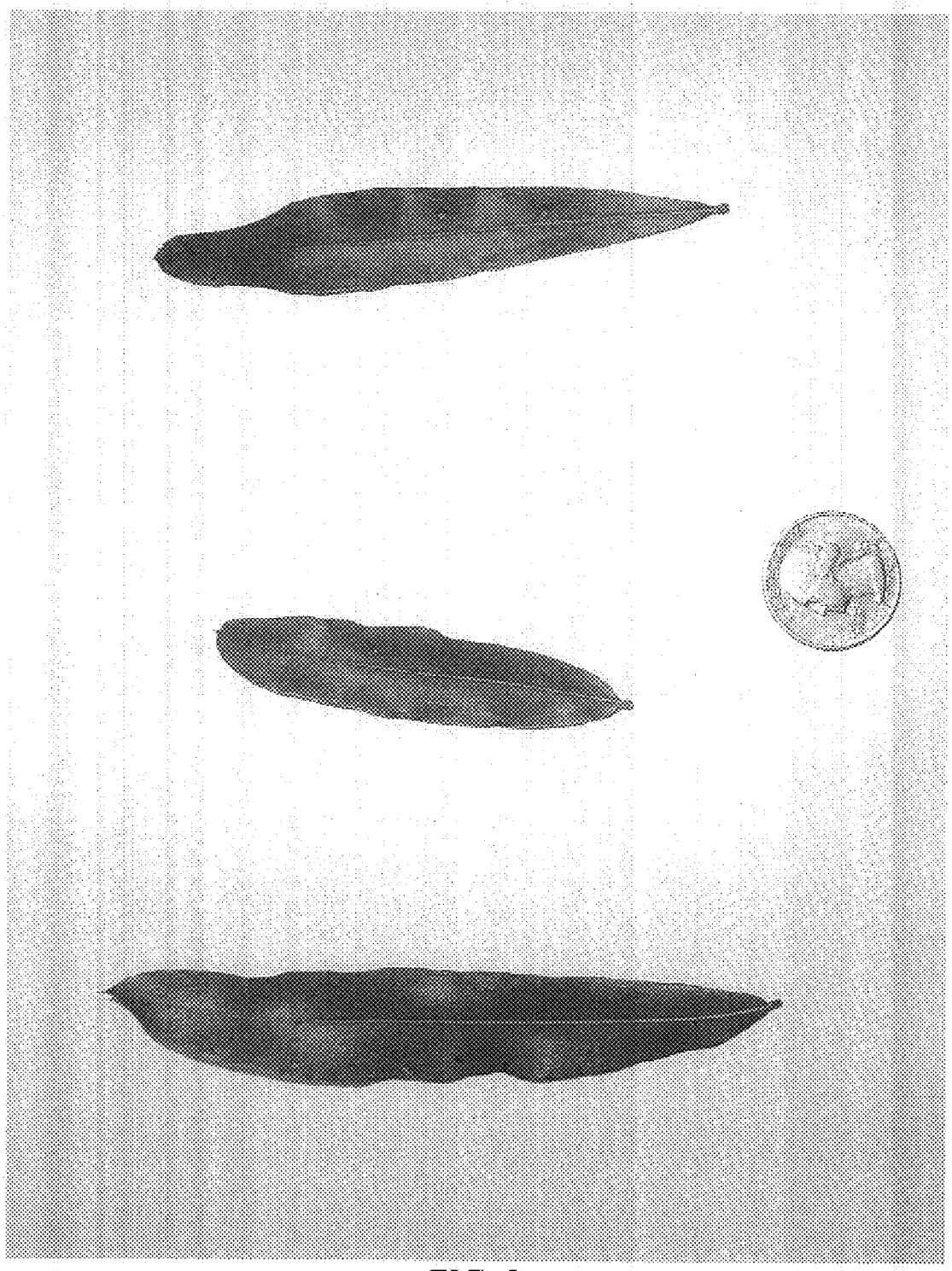
FIG. 3 is a close-up of the top side of three single leaves from a tree of the new variety. The US Quarter Dollar in the picture provides a sizing reference.
Figure 4:
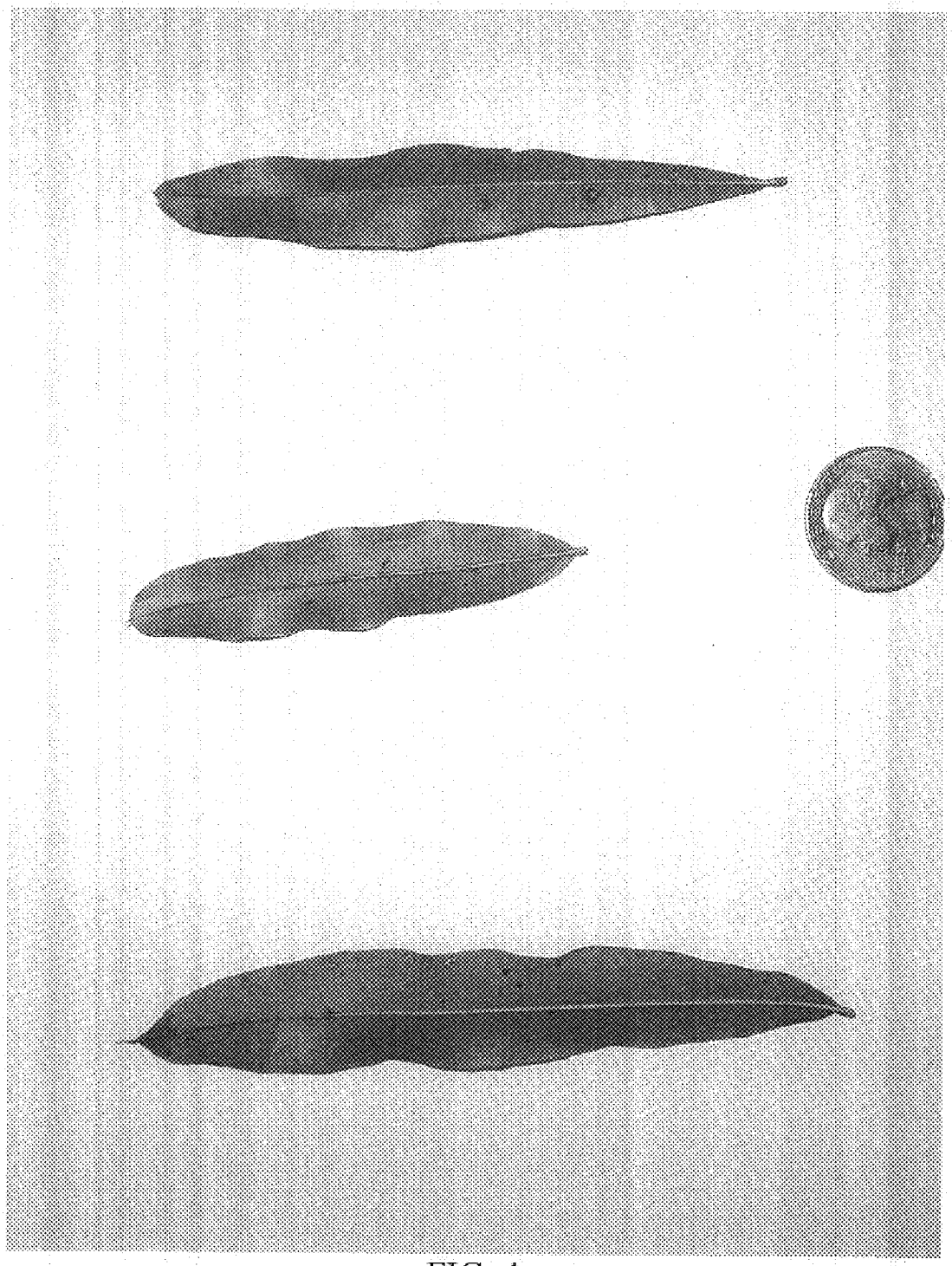
FIG. 4 is a close-up of the underside of three single leaves of the new variety.
Figure 5:
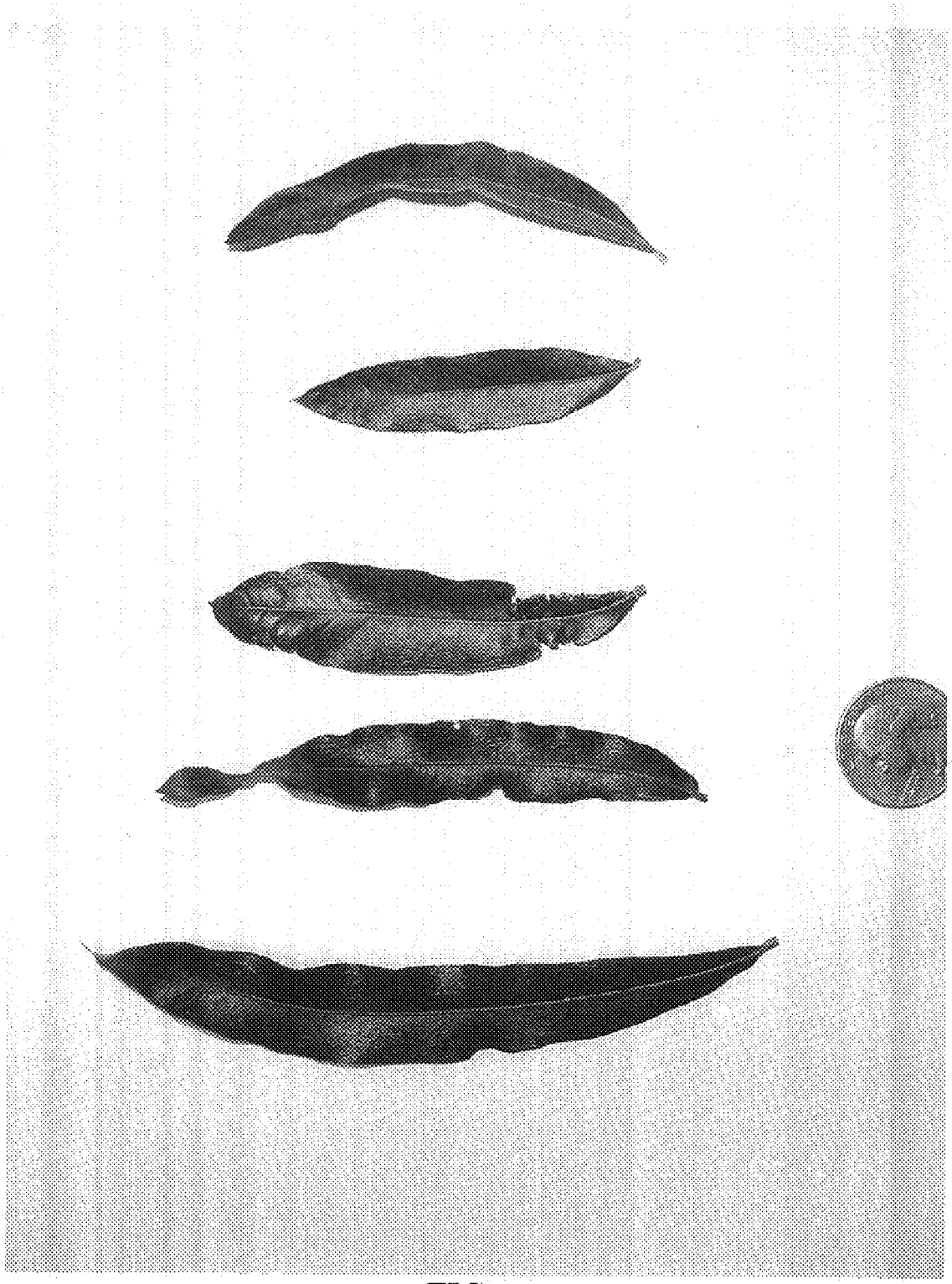
FIG. 5 is a close-up of the top side of five single leaves showing typical fall leaf color of the new variety.
Figure 6:
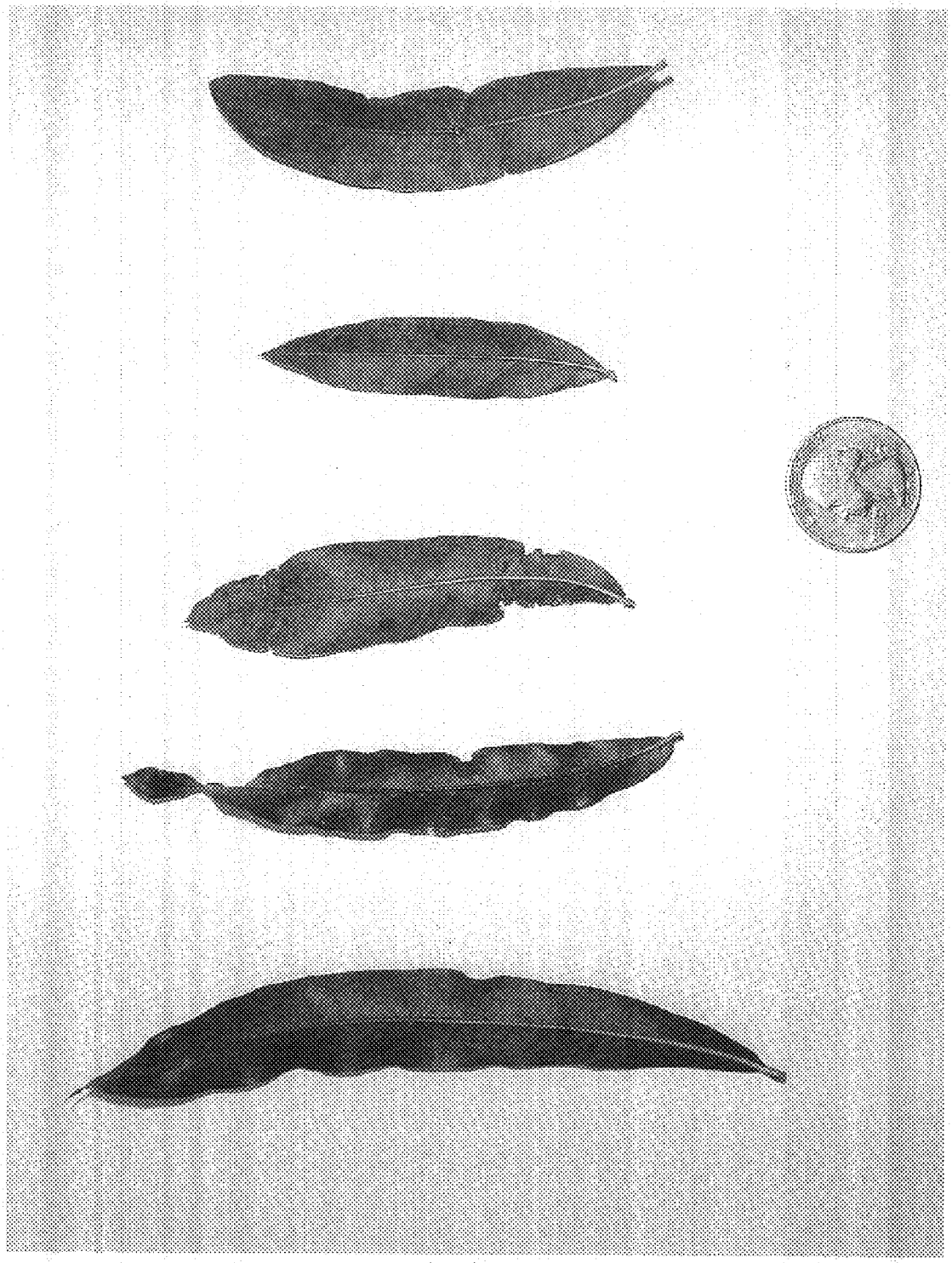
FIG. 6 is a close-up of the underside of five single leaves showing typical fall leaf color of a new variety.

Foliage: Typical of the species. Leaves are alternate, simple; narrowly elliptical or lance-shaped, 2 to 5½ inches long, ⅓ to 1 inch wide; acute, slightly wavy and entire on margins, usually tipped with a bristle. Both the leaf apex and base are acute in shape. Leaves exhibit a pinnate venation pattern with light-green (RHS 145B) colored veins. Leaves emerge light green (RHS 151A) in spring, becoming darker green (RHS 131D) in summer. On mature leaves, the upper leaf surface (FIG. 3) is dark green (RHS 131D), and the lower leaf surface (FIG. 4) is a slightly lighter green (RHS 141D). Fall color (FIGS. 5 (upper) and 6 (lower)) ranges from a red (RHS 47B) to almost a maroon (RHS 46A) color. A typical petiole is approximately ¼ to ⅜ inch long, approximately 1/16 inch in thickness (diameter), and light green (RHS 145B) in color.

*Overall shape.*—Needle-like.

*Base.*—Pointed, less so than apex.

*Apex.*—Sharply pointed.

*Surface texture.*—Smooth, glaucous.

Buds: Typical of the species, being imbricate, ⅛ to ¼ inch long, ovoid, sharp-pointed, chestnut brown (RHS 200D) in color.

Flowers: Typical of the species. Willow Oaks, including the variety, are monoecious. Staminate catkins are pendent and clustered. Individual flowers are typically 4- to 7-lobed calyx enclosing about 6 or more stamens. Pistillate flowers are solitary or borne in spikes from axils of new leaves. Individual flowers usually consist of a 6-lobed calyx surrounding an ovary, the whole being partly enclosed in an involucre. Date of initial bloom (in Oconee County, Ga. is approximately April 1, with duration of approximately 10–14 days.

Fruit: Typical of the species. The acorn, to date observed only in the original tree, is solitary or paired, about ½ inch or less long and wide, subglobose, enclosed at the base by a thin saucer like cap. The acorn itself has alternating brown (RHS 177A) and black (RHS 200A) bands.

Root system: Typical of the species. Oaks typically have coarse root systems, but Willow Oak trees, including the new variety, have a more fibrous root system than other species within the genus.

Pest and disease resistance: Appears to be typical of the species; however, it has shown to be more spider mite resistant.

Winter hardiness: Not yet determined, due to only being grown and observed in Oconee County, Ga. (USDA Zone 7).

I claim:

1. A new and distinct variety of Willow Oak tree named 'QPSTB,' substantially as herein illustrated and described, characterized particularly as to novelty by its dense canopy, dominant central leader, unique red fall color, and relatively fast growth rate.

* * * * *